US010022345B2

(12) United States Patent
Tanaka et al.

(10) Patent No.: US 10,022,345 B2
(45) Date of Patent: Jul. 17, 2018

(54) AGENT FOR PREVENTING AND/OR TREATING VEISALGIA

(71) Applicant: SBI Pharmaceuticals Co., Ltd., Tokyo (JP)

(72) Inventors: Tohru Tanaka, Tokyo (JP); Motowo Nakajima, Tokyo (JP); Fuminori Abe, Tokyo (JP); Satofumi Kawata, Tokyo (JP)

(73) Assignee: SBI PHARMACEUTICALS CO., LTD., Tokyo (JP)

( * ) Notice: Subject to any disclaimer, the term of this patent is extended or adjusted under 35 U.S.C. 154(b) by 0 days.

(21) Appl. No.: 14/954,171

(22) Filed: Nov. 30, 2015

(65) Prior Publication Data

US 2016/0081957 A1 Mar. 24, 2016

Related U.S. Application Data

(63) Continuation of application No. 14/361,187, filed as application No. PCT/JP2012/081080 on Nov. 30, 2012, now abandoned.

(30) Foreign Application Priority Data

Dec. 7, 2011 (JP) .................................. 2011-267841

(51) Int. Cl.

| A61K 31/197 | (2006.01) |
| A61K 33/24 | (2006.01) |
| A61K 33/26 | (2006.01) |
| A61K 33/30 | (2006.01) |
| A61P 25/32 | (2006.01) |
| A61K 31/194 | (2006.01) |
| A61K 31/198 | (2006.01) |
| A61K 31/525 | (2006.01) |
| A61K 33/04 | (2006.01) |
| A61K 31/295 | (2006.01) |
| A61K 31/315 | (2006.01) |
| C07C 229/22 | (2006.01) |
| A61K 9/48 | (2006.01) |

(52) U.S. Cl.
CPC .......... *A61K 31/197* (2013.01); *A61K 31/194* (2013.01); *A61K 31/198* (2013.01); *A61K 31/295* (2013.01); *A61K 31/315* (2013.01); *A61K 31/525* (2013.01); *A61K 33/04* (2013.01); *A61K 33/24* (2013.01); *A61K 33/26* (2013.01); *A61K 33/30* (2013.01); *C07C 229/22* (2013.01); *A61K 9/48* (2013.01)

(58) Field of Classification Search
CPC ..... A23L 1/304; A23L 1/3051; A23K 1/1758; A23K 1/1634; A23K 1/1753; A61K 31/197; C07C 229/22
See application file for complete search history.

(56) References Cited

U.S. PATENT DOCUMENTS

| 2005/0148674 A1* | 7/2005 | Tang ...................... A61K 31/13 514/665 |
| 2008/0026075 A1 | 1/2008 | Kondo et al. |
| 2014/0186464 A1 | 7/2014 | Kinoshita et al. |
| 2014/0249217 A1 | 9/2014 | Rii et al. |

FOREIGN PATENT DOCUMENTS

| CN | 102014890 A | 4/2007 |
| CN | 101010076 A | 8/2007 |
| EP | 1785132 A1 | 5/2007 |
| JP | 2007192659 A | 8/2007 |
| JP | 2009143939 A | 7/2009 |
| WO | WO 2006/025286 A1 | 9/2006 |
| WO | WO 2011161220 A1 | 12/2011 |

OTHER PUBLICATIONS

Definition of prevent, Princeton University "About WordNet." WordNet. Princeton University. 2010. <http://wordnet.princeton.edu>, accessed Sep. 18, 2012.*
Russian Office Action corresponding to Application 2014126564, dated Feb. 16, 2016, 4 pages.
Uzhegov G.N., *Complete Encyclopedia of Premedical Care*, OLMA Media Group, Moscow 2006, Life and Health, p. 105-106.
Chinese First Office Action corresponding to Chinese Application No. 201280059096.9; dated Jul. 3, 2015, 19 pages.
Cho et al., Effect of Evodiae fructus extracts on gene expressions related with alcohol metabolism and antioxidation in ethanol-loaded mice, Food and Chemical Toxicology, vol. 43, 2005, pp. 1365-1371.
D. A. Kharkevich /Pharmacology/College textbook, Moscow 2005, pp. 60.
International Search Report Corresponding to International Application No. PCT/JP2012/081080; dated Feb. 5, 2013; 2 Pages.
Lee et al., Effects of a Preparation of Combined Glutathione-Enriched Yeast and Rice Embryo/Soybean Extracts on Ethanol Hangover, Journal of Medicinal Food, vol. 12(6), 2009, pp. 1359-1367.
Li Yanlin, et al., "Bright Prospects of SOD", Journal of Jixi University, vol. 1(3), Sep. 2001, pp. 48-50.
Mechanism for the Extracts of Tupistra Chinensis Bak. And Balanophora involucrate HK.f. in inhibit alcoholism, Tang Zichun, et al., Lishizhen Medicine and Materia Medica Research, vol. 18 (12), pp. 2958-2960, Dec. 2007.
Office Action corresponding to Russian Patent Application No. 2014126564.
Park et al., Electrolyzed-reduced water inhibits acute ethanol-induced hangovers in Sprague-Dawley rats, Biomedical Research, vol. 30(5), 2009, pp. 263-269.
Japan's Specification and Standards for Food Additives 7th Edition, Ministry of Health and Welfare, 2000, http://www.ffcr.or.jp/zaidan/FFCRHOME.nsf/pages/spec.stand.fa-c-monographs, last updated Nov. 30, 2006, accessed Jul. 9, 2015.

(Continued)

*Primary Examiner* — Irina Neagu
(74) *Attorney, Agent, or Firm* — Myers Bigel, P.A.

(57) ABSTRACT

The object of the present invention is to provide a hangover prophylactic and/or therapeutic agent. The present invention provides a hangover prophylactic and/or therapeutic agent comprising ALAs.

20 Claims, No Drawings

(56) References Cited

OTHER PUBLICATIONS

Kim Min Hee et al. "Effect of black garlic on acute alcohol-induced hangover and chronic alcohol-induced liver injury in rates", *FASEB Journal*, vol. 23, Apr. 2009, p. 111.6.

Pittler et al. "Interventions for preventing or treating alcohol hangover: systematic review of randomised controlled trials", *BMJ* 331(7531):1515-8 (2005).

Costa, C. et al. "Correlation between plasma 5-aminolevulinic acid concentrations and indicators of oxidative stress in lead-exposed workers", *Clin. Chem.*, 43(7):1196-1202 (1997).

Demasi, M. et al. "The Prooxidant Effect of 5-Aminolevulinic Acid in the Brain Tissue of Rats: Implications in Neuropsychiatric Manifestations in Porphyrias", *Free Radical Biol. Med.*, 20(3)291-299 (1996).

Ito, S. et al. "Enhancement of 5-Aminolevulinic acid-induced oxidative stress on two cancer cell lines by gold nanoparticles", *Free Radical Res.*, 43(12):1214-1224 (2009).

Karbownik, M. et al. "Renal toxicity of the carcinogen d-aminolevulinic acid: antioxidant effects of melatonin", *Cancer Letters*, 161:1-7 (2000).

Noriega, G. et al. "Bilirubin is highly effective in preventing in vivo γ-aminolevulinic acid-induced oxidative cell damage", *Biochim. Biophys. Acta*, 1638:173-178 (2003).

Pereira, B. et al. "5-aminolevulinic acid-induced alterations of oxidative metabolism in sedentary and exercisetrained rats", *J. Appl. Physiol.* 70:221-226 (1992) abstract only.

Princ, FG et al. "Melatonin's antioxidant protection against 8-aminolevulinic acid-induced oxidative damage in rat cerebellum", *J. Pineal Res.*, 23:40-46 (1997).

Verster, JC et al. "Treatment and prevention of alcohol hangover", *Curr. Drug Abuse Rev.*, 3(2):116-126 (2010).

Weiss, T. et al. "Cellular damage to human hepatocytes through repeated application of 5-aminolevulinic acid", *J. Hepatology*, 38:476-482 (2003).

\* cited by examiner

AGENT FOR PREVENTING AND/OR TREATING VEISALGIA

STATEMENT OF PRIORITY

This application is a continuation application of, and claims priority to, U.S. patent application Ser. No. 14/361,187, filed May 28, 2014, which is a 35 U.S.C. § 371 national phase application of International Application Serial No. PCT/JP2012/081080, filed Nov. 30, 2012, which claims the benefit of Japanese Patent Application No. 2011-267841, filed Dec. 7, 2011, the entire contents of each of which are incorporated by reference herein.

TECHNICAL FIELD

The present invention relates to a hangover prophylactic and/or therapeutic agent. More specifically, the present invention relates to a hangover prophylactic and/or therapeutic agent comprising ALAs.

BACKGROUND ART

Alcohol beverages, being important beverages that improve communication in human society, are essential for social life. This is also clear from the fact that alcohol beverages are offered at many religious or ceremonial functions. It is not too much to say that alcohol beverages are a part of the culture.

However, it is also a clear fact that excess alcohol intake imposes a burden on health and economy. Illnesses thought to be caused by excess intake of alcohol beverages represent 9% of all illnesses, and there is also a report stating that the loss reaches 7 trillion yen per year in Japan. To this report, there is also a counterargument that positive effects brought about by moderate alcohol beverage intake are not evaluated, and a quantitative evaluation of health hazards is challenging.

Meanwhile, alcohol beverage intake, if not directly causes health hazards, clearly generates one's malfunction or social losses due to hangovers. In a research in England, social losses limited, to work absences due to hangovers are calculated at 240 billion yen.

From such background, a method for pleasantly consuming alcohol beverages without having a hangover is not simply a desire of alcohol drinkers but also a social demand.

As a prophylactic measure of hangovers, investigations with pharmaceuticals such as tolfenamic acid have been performed. In addition, investigations by natural ingredients such as dry yeast, prickly pear, and turmeric have also been performed as a prophylactic measure of hangovers. Although there is also a report stating that a certain effect was identified for prickly pear, it is also clear that its effect is insufficient since it has shown no signs of gaining popularity.

Acetaldehyde which is an ethyl alcohol metabolism intermediate is said to be the main cause of hangovers. Accordingly, low enzyme activity of aldehyde dehydratase is said to be the cause of hangovers. However, since for example hangover symptoms are diverse and symptoms vary depending on the type of alcohol beverage, the mechanism of hangover cannot be described merely by acetaldehyde.

Moreover, although it is common to be thought that the cause of hangover is attributed to the liver function since many of drug metabolisms take place in the liver, in light of the fact that the two major symptoms of hangovers are retching and headache, it cannot be deemed that improvement of liver function by itself will allow prevention of hangovers.

The development of a truly effective hangover prophylactic and/or therapeutic agent has been much awaited from drinkers as well as as a social demand.

SUMMARY OF THE INVENTION

Technical Problem

The object of the present invention is to provide an effective hangover prophylactic and/or therapeutic agent.

Solution to Problem

A hangover generally refers to the overall physical failure that lingers after the direct effects of alcohol on the brain or nerve accompanying alcohol intake, and examples of major symptoms include nausea, retching, headache, stomachache, thirst, weakness, and exacerbation of skin symptoms.

The present inventors noted that there are individual differences in the extent of hangovers, and hypothesized that the difference in the production amount of endogenous substances leads to the individual difference in the extent of hangovers. As a result of broadly searching endogenous substances, the inventors themselves also participating in trials, and after repeated investigations, the inventors quite surprisingly found that ALAs have the effect of preventing and/or treating a hangover.

ALA herein means 5-aminolevulinic acid. ALA is also called δ-aminoievulinic acid, and is a type of amino acid. ALA is an in vivo endogenous substance, and is known as a heme precursor. ALA is known for various bioactivities, and is broadly employed in Photo Dynamic Therapy (PDT) and Photo Dynamic Diagnosis (PDD) in the diagnostic or therapeutic fields of cancer etc. Although ALA is a common precursor of heme compounds, it is known that in cancer cells, heme is not produced even when ALA is administered and a heme compound precursor protoporphyrin IX (PPIX) is accumulated. PDD becomes possible because fluorescence is emitted when light is irradiated on the accumulated PPIX. Moreover, in the presence of oxygen, PDT becomes possible because reactive oxygen is produced when light is irradiated on the accumulated PPIX. However, in regard to the relationship between ALA and PDT or PDD effects and hangover prophylactics and/or therapeutics, the connection can in no way be anticipated.

ALA is also known to be a heme precursor and effective for prevention of anemia. However, a non-anemic person will also have a hangover, and there is no report stating that an anemic person is susceptible to a hangover.

Although ALA is known to improve sugar or lipid metabolism, since the cause of hangover is presently unknown as previously described, it cannot be envisioned from existing information that ALA is effective for prevention of hangovers.

The present inventors, after numerous extensive investigations, have established, a hangover prophylactic and/or therapeutic agent comprising ALAs to complete the present invention (the elucidation of the exact mechanism regarding why ALAs are effective for hangovers, however, is a challenge for future science). The present inventors also carried out numerous extensive investigations regarding combinations with further other ingredients (pharmaceutical ingredients and/or non-pharmaceutical ingredients) as well as the dosage or administration method etc.

In other words, the present invention relates to a hangover prophylactic and/or therapeutic agent comprising a compound shown below (Formula I):

[Chemical Formula 1]

$R^1$—NHCH$_2$COCH$_2$CH$_2$COOR$^2$ (Formula I)

(wherein $R^1$ represents a hydrogen atom or an acyl group, and $R^2$ represents a hydrogen atom, a linear or branched alkyl group, a cycloalkyl group, an aryl group, or an aralkyl group)
or a salt, thereof.

In the above (Formula I), the hangover prophylactic and/or therapeutic agent of the present invention may be those wherein:

$R^1$ is selected from the group consisting of a hydrogen atom, an alkanoyl group having 1-8 carbons, and an aroyl group having 7-14 carbons, and $R^2$ is selected from the group consisting of a hydrogen atom, a linear or branched alkyl group having 1-8 carbons, a cycloalkyl group having 3-8 carbons, an aryl group having 6-14 carbons, and an aralkyl group having 7-15 carbons.

In the above (Formula I), the hangover prophylactic and/or therapeutic agent of the present invention may be those wherein:

$R^1$ is selected from the group consisting of a hydrogen atom, a formyl group, an acetyl group, a propionyl group, and a butyryl group, and $R^2$ is selected from the group consisting of a hydrogen atom, a methyl group, an ethyl group, a propyl group, a butyl group, and a pentyl group.

In the above (Formula I), the hangover prophylactic and/or therapeutic agent of the present invention may be those wherein:

$R^1$ is a hydrogen atom, and $R^2$ is selected from the group consisting of a hydrogen atom, a methyl group, an ethyl group, a propyl group, a butyl, group, and a pentyl group.

In the above (Formula I), the hangover prophylactic and/or therapeutic agent of the present invention may be those wherein:

$R^1$ is a hydrogen atom, and $R^2$ is a hydrogen atom.

The hangover prophylactic and/or therapeutic agent of the present invention may further contain one or two or more types of metals. In addition, said metal may be selected from the group consisting of iron, magnesium, zinc, nickel, vanadium, copper, chromium, molybdenum, and cobalt. Moreover, said metal may be, among others, selected, from the group consisting of iron, magnesium, and zinc. Moreover, when iron is employed, sodium ferrous citrate may be employed.

The present invention also relates to a method for preventing and/or treating a hangover, characterized in administering the hangover prophylactic and/or therapeutic agent of the present invention.

Advantageous Effects of Invention

The present invention provides a hangover prophylactic and/or therapeutic agent. Therapy herein includes not only complete elimination of hangover symptoms, but also improvement of hangover symptoms. Similarly, in regards to prevention, the term includes not only completely stopping hangover symptoms from occurring, but also further mitigating hangover symptoms that would otherwise have occurred if the prophylactic agent of the present invention was not administered. By using the agent of the present invention, a superior hangover prophylactic and/or therapeutic effect without almost any side effect can be achieved. In this way, the agent of the present invention is not only beneficial for alcohol drinkers, but can also reduce social losses produced by hangovers.

DESCRIPTION OF EMBODIMENTS

The hangover prophylactic and/or therapeutic agent of the present invention is not particularly limited as long as it is a hangover prophylactic and/or therapeutic agent containing ALAs. The agent of the present invention can be ingested before alcohol consumption, ingested during alcohol consumption, or ingested after alcohol consumption, or also ingested after development of a hangover as appropriate according to embodiments.

The compound employed as the hangover prophylactic and/or therapeutic agent of the present invention is ALAs. ALAs herein refer to an ALA or a derivative thereof or a salt thereof.

An ALA derivative can be exemplified by a compound represented below (Formula I). In (Formula I), $R^1$ represents a hydrogen atom or an acyl group, and $R^2$ represents a hydrogen atom, a linear or branched alkyl group, a cycloalkyl group, an aryl group, or an aralkyl group. In (Formula I), ALA corresponds to the case where $R^1$ and $R^2$ are a hydrogen atom.

[Chemical Formula 2]

$R^1$—NHCH$_2$COCH$_2$CH$_2$COOR$^2$ (Formula I)

ALAs may only need to act in vivo as an active ingredient in the state of the ALA of (Formula I) or a derivative thereof, or it can also be administered as a prodrug (precursor) that is degraded by an in vivo enzyme.

The acyl group in $R^1$ of (Formula I) can include a linear or branched alkanoyl group having 1-8 carbons such as formyl, acetyl, propionyl, butyryl, isobutyryl, valeryl, isovaleryl, pivaloyl, hexanoyl, octanoyl, and benzylcarbonyl groups, as well as an aroyl group having 7-14 carbons such as benzoyl, 1-naphthoyl, and 2-naphthoyl groups.

The alkyl group in $R^2$ of (Formula I) can include a linear or branched alkyl group having 1-8 carbons such as methyl, ethyl, propyl, isopropyl, butyl, isobutyl, sec-butyl, tert-butyl, pentyl, isopentyl, neopentyl, hexyl, heptyl, and octyl groups.

The cycloalkyl group in $R^2$ of (Formula I) can include a saturated cycloalkyl group having 3-8 carbons such as cyclopropyl, cyclobutyl, cyclopentyl, cyclohexyl, cycloheptyl, cyclooctyl, cyclododecyl, and 1-cyclohexenyl group, or those which may partially have unsaturated bonds present.

The aryl group in $R^2$ of (Formula I) can include an aryl group having 6-14 carbons such as phenyl, naphthyl, anthryl, and phenanthryl groups.

As the aralkyl group in $R^2$ of (Formula I), the aryl moiety can be exemplified as the same as the aryl group above, and the alkyl moiety can be exemplified as the same as the alkyl group above. Specifically, an aralkyl group having 7-15 carbons such as benzyl, phenethyl, phenylpropyl, phenylbutyl, benzhydryl, trityl, naphthylmethyl, and naphthylethyl groups can be included.

Preferred ALA derivatives include compounds in which $R^1$ is e.g. a formyl group, an acetyl group, a propionyl group, or a butyryl group. Moreover, preferred ALA derivatives include compounds in which the above $R^2$ is e.g. a methyl group, an ethyl group, a propyl group, a butyl group, or a pentyl group. Moreover, preferred ALA derivatives include compounds in which the combination of the above $R^1$ and $R^2$ is each combination of (formyl and methyl), (acetyl and methyl), (propionyl and methyl), (butyryl and methyl), (formyl and ethyl), (acetyl and ethyl), (propionyl and ethyl), and (butyryl and ethyl).

Among ALAs, examples of a salt, of ALA or a derivative thereof can include a pharmaceutically acceptable acid addition salt, a metal salt, an ammonium salt, and an organic amine addition salt. Acid addition salts can be exemplified by e.g. each of inorganic acid salts such as hydrochloride, hydrobromide, hydroiodide, phosphate, nitrate, and sulfate salts, and each of organic acid addition salts such as formate, acetate, propionate, toluenesulfonate, succinate, oxalate, lactate, tartrate, glycolate, methanesulfonate, butyrate, valerate, citrate, fumarate, maleate, and malate salts. Metal salts can be exemplified by each of alkali metal salts such as lithium, sodium, and potassium salts, each of alkaline earth metal salts such as magnesium and calcium salts, and each of metal salts such as aluminum and zinc. Ammonium salts can be exemplified by e.g. alkyl ammonium salts such as an ammonium salt and a tetramethylammonium salt. Organic amine salts can be exemplified by each of salts such as a triethylamine salt, a piperidine salt, a morpholine salt, and a toluidine salt. These salts can also be employed as a solution upon use.

Among the above ALAs, the most desirable are ALA and various esters such as an ALA methyl ester, an ALA ethyl ester, an ALA propyl ester, an ALA butyl ester, and an ALA pentyl ester, as well as hydrochloride, phosphate, and sulfate salts thereof. Among these, an ALA hydrochloride salt and an ALA phosphate salt can be exemplified as particularly preferable.

The above ALAs can be manufactured by e.g. a well-known method such as chemical synthesis, production by microorganisms, and production by enzymes. Moreover, the above ALAs may also form a hydrate or a solvate, and ALAs can be employed alone or in an appropriate combination of two or more.

The hangover prophylactic and/or therapeutic agent of the present invention is preferably those further containing a metal in the range that does not cause excess symptom, and a metal compound can be advantageously employed as such a metal as long as it does not adversely affect the effects of the present invention. The metal in the present invention can include iron, magnesium, zinc, nickel, vanadium, cobalt, copper, chromium, and molybdenum, preferably iron and zinc.

Iron compounds can include e.g. ferrous citrate, sodium ferrous citrate, iron sodium citrate, iron ammonium citrate, ferric pyrophosphate, heme iron, iron dextran, iron lactate, ferrous gluconate, iron sodium diethylenetriamine pentaacetic acid, iron ammonium diethylenetriamine pentaacetic acid, iron sodium ethylenediamine tetraacetic acid, iron ammonium ethylenediamine pentaacetic acid, triethylenetetramine iron, iron sodium dicarboxymethylglutamate, iron ammonium ammonium dicarboxymethylglutamate, iron lactoferrin, iron transferrin, ferric chloride, iron sesquioxide, sodium iron chlorophyllin, ferritin iron, ferrous fumarate, ferrous pyrophosphate, saccharated iron oxide, iron acetate, iron oxalate, ferrous succinate, iron and sodium succinate citrate, iron sulfate, and ferrous glycine sulfate, among which ferrous citrate and sodium ferrous citrate are preferred.

Zinc compounds can include zinc chloride, zinc oxide, zinc nitrate, zinc carbonate, zinc sulfate, zinc diaramonium diethylenetriamine pentaacetic acid, zinc disodium ethylenediamine tetraacetic acid, zinc protoporphyrin, and zinc-containing yeast.

One or two or more types of each of the above metals can be employed, and the dosage of the metal can be exemplified as 0.01-10 folds, preferably 0.1-5 folds, and more preferably 0.2-2 folds of the ALAs dosage in molar ratio.

The ALAs and the metal contained in the hangover prophylactic and/or therapeutic agent of the present invention can also be administered as a composition comprising ALAs and metal or each alone, but it is preferred that they are simultaneously administered even when they are each administered alone. However, the administration of the ALAs and the metal, even if not strictly simultaneous, may be performed without a substantial interval between the two so that an additive or a synergistic effect can be exerted.

Examples of the administration route of the hangover prophylactic and/or therapeutic agent of the present invention can include oral administrations including sublingual administration, inhalation administration, intravenous administration including infusion, transdermal administration by e.g. a patch, and parenteral administration such as administration by forced enteral nutrition method employing a suppository or a nasogastric tube, a nasointestinal tube, a gastrostomy tube, or an enterostomy tube, although oral administration is common.

The dosage form of the hangover prophylactic and/or therapeutic agent of the present invention can be appropriately determined according to the above administration route, examples of which can include an injection, an infusion, a tablet, a capsule, fine granules, powders, a liquid, a liquor dissolved in e.g. a syrup, a poultice, and a suppository.

In order to prepare the hangover prophylactic and/or therapeutic agent of the present invention, a carrier, an excipient, a diluent, an additive, a disintegrant, a binder, a coating, a lubricant, a glider, a lubricant, a flavoring agent, a sweetening agent, a solubilizer, a solvent, a gelling agent, and a nutrient, etc. which may be pharmacologically acceptable can be added as necessary, specific examples of which can be water, saline, animal fat and oil, vegetable oil, lactose, starch, gelatin, crystalline cellulose, gum, talc, magnesium stearate, hydroxypropylcellulose, polyalkylene glycol, polyvinyl alcohol, and glycerin. When the hangover prophylactic and/or therapeutic agent of the present invention is to be prepared as an aqueous solution, attention must be paid so that the aqueous solution will not become alkaline in order to prevent degradation of ALAs. In the case it becomes alkaline, degradation can also be prevented by removing oxygen.

The amount, the frequency, and the duration of the hangover prophylactic and/or therapeutic agent of the present invention will vary according to the age, weight, and symptoms etc. of the person who will be utilizing the hangover prophylactic agent. Examples of the preferred, dosage can include 1 mg-3000 rag, preferably 2 mg-1000 mg, more preferably 3 mg-700 mg, and further preferably 5-200 mg per adult of ALA phosphate salt equivalent. The preferred dosage can also be calculated when employing other ALAs by calculating the molar equivalency. Naturally, the above preferred dosage range is merely an exemplification and is not limiting.

The administration timing may be any of before alcohol consumption, at the start of alcohol consumption, during alcohol consumption, after alcohol consumption, and after development of a hangover, and the ingestion may be divided into multiple timings of these. When the ingestion is before alcohol consumption, it is desirably within 24 hours, desirably within 12 hours, and further desirably within 6 hours before alcohol consumption.

The hangover prophylactic and/or therapeutic agent of the present invention can also be used in combination with other existing hangover prophylactic and/or therapeutic agents. Examples of existing hangover prophylactic and/or therapeutic agents include e.g. dichloroacetic acid, aspirin, malic acid, caffeine, prickly pear extract, lime tree extract, and turmeric. Since the mechanisms related to these agents and the ALA hangover prophylactic and/or therapeutic agent are thought to be each fundamentally different, additive or in some cases synergetic effects can be expected.

The present invention will be more specifically described by Examples below, but the technological range of the present invention is not to be limited to these exemplifications.

EXAMPLES

Example 1

Ten test subjects shown in Table 1 ingested a capsule comprising 50 mg of aminolevulinic acid phosphate salt and 57.4 mg of sodium ferrous citrate after lunch, and consumed alcohol in the evening. The test subject shown by the same alphabet A-J in other Examples means the identical test subject. Each test subject was asked to consume beverages containing alcohol in amounts thought to be appropriate, and then further consume approximately 180 ml of Japanese sake in addition. Subsequently, feedbacks in regards to the condition of each test subject on the "same day after alcohol consumption" and the "morning after alcohol consumption" were taken from each test subject on the day after alcohol consumption. The results are shown in Table 2. It is apparent from Table 2 that the agent of the present invention has a hangover prophylactic effect. Moreover, Table 2 also shows that there is a tendency for the amount of possible alcohol intake to increase by ingesting the agent of the present invention before alcohol consumption.

TABLE 1

Profile of Test Participants

|   | Age | Sex | Occupation | Alcohol consumption status |
|---|---|---|---|---|
| A | 50 | Male | Company employee | Almost everyday |
| B | 60 | Male | Company employee | Almost everyday |
| C | 44 | Male | Company employee | Almost everyday |
| D | 47 | Male | Company employee | Approximately 5 days/week |
| E | 36 | Male | Company employee | Approximately 3 days/week |
| F | 42 | Male | Company employee | Does not usually drink |
| G | 40 | Female | Company employee | Approximately a day/week |
| H | 36 | Female | Company employee | Approximately 5 days/week |
| I | 35 | Female | Company employee | Approximately 4 days/week |
| J | 33 | Female | Company employee | Approximately 3 s/week |

TABLE 2

Test Results 1

|   |   |   |
|---|---|---|
|   | 1) | Amount of alcohol intake |
|   | 2) | Condition on same day after alcohol consumption |
|   | 3) | Condition on morning after alcohol consumption |
| A | 1) | 500 ml of beer, approximately 720 ml of Japanese sake |
|   | 2) | Subject usually experiences retching when consuming approximately 540 ml or more of Japanese sake, but was all right. |
|   | 3) | Subject usually has a headache the next day when drinking this much, but was surprised to be in excellent condition. |
| B | 1) | 500 ml of beer, approximately 540 ml of Japanese sake |
|   | 2) | Subject does not respond so well to Japanese sake, but was able to drink it comfortably. |
|   | 3) | Subject had no hangover at all. |
| C | 1) | 500 ml of beer, approximately 1080 ml of Japanese sake |
|   | 2) | Subject was very well drunk, but felt capable of drinking more. |
|   | 3) | Subject woke up feeling good, and arrived at the office by 7 o'clock which is earlier than usual. |
| D | 1) | 500 ml of beer, approximately 720 ml of Japanese sake |
|   | 2) | Subject felt that he was unsteady on the feet and clearly drunk but maintained clear conscience. |
|   | 3) | Subject was worried if going to work was possible the next day by drinking this much, but was all right. |
| E | 1) | 1000 ml of beer, approximately 360 ml of Japanese sake |
|   | 2) | Subject falls asleep when drinking Japanese sake, but was perfectly fine. |
|   | 3) | Subject often has a headache and a stomachache the day after drinking Japanese sake, but was fine. |
| F | 1) | 500 ml of beer, approximately 180 ml of Japanese sake |
|   | 2) | Subject was never able to drink this much before. |
|   | 3) | Subject went home after declaring to possibly miss work, but was fine. |
| G | 1) | 500 ml of beer, approximately 540 ml of Japanese sake |
|   | 2) | Maximum record for Japanese sake. Subject did not feel sick. |
|   | 3) | Subject was worried about the skin condition the next day by drinking this much, but it was rather better than usual. |
| H | 1) | 1000 ml of beer, approximately 360 ml of Japanese sake |
|   | 2) | Subject typically feels fine while drinking, so it was as usual. |
|   | 3) | Subject is typically vulnerable the next day, but surprised to feel fine regardless of drinking more than usual. |
| I | 1) | 2000 ml of beer, approximately 180 ml of Japanese sake |
|   | 2) | Subject is weak with anything but beer, but fine with Japanese sake. |
|   | 3) | Subject was surprised that there was no heavy sensation in the head that is usually experienced the day after drinking. |
| J | 1) | 500 ml of beer, approximately 540 ml of Japanese sake |
|   | 2) | Maximum record for Japanese sake. Subject was able to drink comfortably. |
|   | 3) | Subject had an upset stomach all the same due to a sensitive stomach, but there was no headache at all. |

Example 2

In this Example, the results of a test carried out similarly to Example 1 except that a capsule was ingested at the start of alcohol consumption are shown in Table 3. As apparent from Table 3, a clear prophylactic effect of hangovers is seen even when ingestion was at the start of alcohol consumption. Moreover, the tendency for the amount of alcohol intake to increase when ingestion was at the start of alcohol consumption was not particularly observed merely from this experiment.

TABLE 3

Test Results 2

|   |   |   |
|---|---|---|
|   | 1) | Amount of alcohol intake |
|   | 2) | Condition on same day after alcohol consumption |
|   | 3) | Condition on morning after alcohol consumption |
| A | 1) | 1000 ml of beer, approximately 540 ml of Japanese sake |
|   | 2) | Subject usually experiences retching when consuming approximately 540 ml or more of Japanese sake, but was all right. |

TABLE 3-continued

Test Results 2

|   |    |                                                                                                                       |
|---|----|-----------------------------------------------------------------------------------------------------------------------|
|   | 3) | Subject usually has a headache the next day when drinking this much, but was surprised to be in excellent condition. |
| B | 1) | 500 ml of beer, approximately 540 ml of Japanese sake                                                                 |
|   | 2) | Subject does not respond so well to Japanese sake, but was able to drink it comfortably.                              |
|   | 3) | Subject had no hangover at all.                                                                                       |
| C | 1) | 500 ml of beer, approximately 900 ml of Japanese sake                                                                 |
|   | 2) | Subject was in excellent condition as usual.                                                                          |
|   | 3) | Subject was in excellent condition as usual.                                                                          |
| D | 1) | 1000 ml of beer, approximately 540 ml of Japanese sake                                                                |
|   | 2) | Subject felt that he was unsteady on the feet and apparently drunk but kept clear conscience.                         |
|   | 3) | Subject still felt drunk when waking up in the morning, but it did not feel like a hangover.                          |
| H | 1) | 1500 ml of beer, approximately 180 ml of Japanese sake                                                                |
|   | 2) | Subject typically feels fine while drinking, so it was as usual.                                                      |
|   | 3) | Subject is typically vulnerable the next day, but able to get up earlier than her husband.                            |

Example 3

In this Example, a capsule comprising 10 mg of aminolevulinic acid phosphate salt, 11.5 mg of sodium ferrous citrate, and 50 mg of zinc yeast (amount of zinc: 5 mg) was ingested at the end of alcohol consumption. The results are shown in Table 4. A clear prophylactic effect of hangovers is seen even when ingestion was after alcohol consumption.

TABLE 4

Test Results 3

|   |    |                                                                                                                       |
|---|----|-----------------------------------------------------------------------------------------------------------------------|
|   | 1) | Amount of alcohol intake                                                                                              |
|   | 2) | Condition on same day after alcohol consumption                                                                       |
|   | 3) | Condition on morning after alcohol consumption                                                                        |
| A | 1) | 500 ml of beer, 1 bottle of red wine                                                                                  |
|   | 2) | Subject started to feel good on the train on the way home, and had another 500 ml of beer at home.                    |
|   | 3) | Subject woke up refreshed in the morning earlier than usual, and was surprised to be in excellent condition.          |
| B | 1) | 500 ml of beer, 1 bottle of white wine, 1 bottle of red wine                                                          |
|   | 2) | Subject was able to drink comfortably as usual.                                                                       |
|   | 3) | Subject had no hangover at all.                                                                                       |
| E | 1) | 1000 ml of beer, 1 bottle of white wine                                                                               |
|   | 2) | Subject falls asleep when drinking wine, but was perfectly fine.                                                      |
|   | 3) | Subject was worried about not able to wake up in the morning, but was surprised to be in rather excellent condition.  |
| I | 1) | 2500 ml of beer                                                                                                       |
|   | 2) | Subject felt she was starting to feel sober by the time she arrived home.                                             |
|   | 3) | Subject felt somehow in a better physical condition than usual, and application of make-up felt smooth.               |

Example 4

Test subject A had too much to drink during a business trip to China and vomited in the middle of the night. He still had a terrible hangover on the morning after alcohol consumption, and could not eat any breakfast. Therefore, one capsule of Example 1 and one capsule of Example 3 were ingested on the morning after alcohol consumption. While lying down, symptoms started to improve after about 30 minutes and the subject had recovered after 2 hours. From past experiences, the subject was useless when drinking enough to vomit on the day before, but he uneventfully performed through a meeting and was able to tolerate a business dinner with alcohol consumption in the evening.

It has become apparent from this case example that the agent of the present invention has an effect of treating a hangover when administered after a hangover is developed. In other words, it is seen that the agent of the present invention is also superior as a hangover therapeutic agent.

Example 5

Test subject D partied too much at a class reunion and developed a terrible hangover. Although he was in no condition to go to work, there was an important meeting in the afternoon. Therefore, he took an aspirin and forced himself to come to the office, but was obliged to get off the train at a way station due to retching and ended up being late. The test subject was unable to work due to retching and headache from hangover even after arriving at work, but upon ingesting two capsules of Example 3 together with a drink containing 5 mg of ALA phosphate salt "Hanamitsu Drink™" (SBI ALApromo Co., Ltd.), he gradually recovered from about 30 minutes after ingestion, and was able to uneventfully organize a meeting the first thing in the afternoon.

It has become apparent from this case example that the agent of the present invention has an effect of treating a hangover when administered after a hangover is developed. In other words, it is seen that the agent of the present invention is also superior as a hangover therapeutic agent.

Example 6

A 33-year-old female who has never felt refreshed from alcohol consumption because of a headache caused even by a small amount of alcohol consumption ingested three tablets of a commercial product "Liverall™" (Daiichi Sankyo Company, Limited) containing isopropylamine dichloroacetate as the active ingredient and two capsules shown in Example 3 at the start of alcohol consumption. As a result, a headache that usually develops at about 30 minutes from the start of alcohol consumption did not develop at all, and she was able to consume 500 ml of draft beer and one glass of plum wine. This female felt refreshed and was able to have an extremely satisfying alcohol consumption experience, gaining a sense of community with other participants. This case example shows that the present agent can also be used in combination with other agents.

Example 7

Test subjects A and C consumed approximately 2,700 ml of Japanese sake between the two. Then, test subjects A and C each ingested two capsules comprising 10 mg of aminolevulinic acid phosphate salt, 11.5 mg of sodium ferrous citrate, 50 mg of zinc yeast (amount of zinc: 5 mg), 6 mg of molybdenum yeast (12 μg of molybdenum), 5 mg of selenium yeast (10 μg of selenium), 1.67 mg of citric acid, 5 mg of malic acid, 0.45 mg of vitamin B2, and 5 mg of L-cystine at the end of alcohol consumption. As a result, neither of the two developed a hangover.

Example 8

Test subject A who consumed Japanese sake similarly to Example 7 without ingesting any capsules developed a terrible hangover condition. Test subject A ingested one capsule comprising 100 mg of aminolevulinic acid. As a result, symptoms started to recover after 30 minutes had passed since administration, and he had completely recovered after 1.5 hours.

Example 9

The following tests were performed to more quantitatively measure that ALAs are effective for the prevention or therapy of a hangover.

In other words, as shown in Table 5 below, a questionnaire was given to fifteen test subjects in regards to (A) the body condition "after alcohol consumption on the day of alcohol consumption" ("after alcohol consumption (same day)" in Table 5) and (B) the body condition on "the morning after the day of alcohol consumption" ("morning after alcohol consumption" in Table 5) for (1) when ALAs was ingested and (2) when ALAs was not ingested. In this experiment, aminolevulinic acid phosphate salt was employed as ALAs.

Each test subject, consumed alcohol in the evening for a total of two times in order to evaluate hangover symptoms in regards to each of (1) when ALAs was ingested and (2) when ALAs was not ingested. In the experiment with ALAs ingestion and the experiment without ALAs ingestion, the order for which of the experiments was performed first and the other of the experiments was performed, later was randomly selected for each test subject. Each experiment was performed with at least a few days apart.

Total amount of alcohol consumption varies by test subject. This is because a moderate amount for each test subject was consumed. Moreover, alcohol consumption was made so that the total amount of the second alcohol consumption was the same as the total amount of the first alcohol consumption (note that as exceptions, (1) the total amount of alcohol consumption when ALAs was ingested and (2) the total amount of alcohol consumption when ALAs was not ingested are not the same for test subjects 1, 2, and 12 in Table 5 below). In Table 5 below, the "total amount of alcohol consumption" indicates a value converted into the total amount of alcohol contained in beer or Japanese sake etc. consumed (in other words, in the case of a 500 ml canned beer, if the alcohol percentage is 5%, it is calculated as 25 mg).

Moreover, for each test subject, the timing of ALAs ingestion (1) when ALAs was ingested was "at the start of alcohol consumption" and/or "after the end of alcohol consumption" as shown in Table 5 below. The ingestion of ALAs (aminolevulinic acid phosphate salt) was performed by selecting at least one from below:

(A) the capsule of Example 1 (contains 50 mg of ALAs),
(B) the capsule of Example 3 (contains 10 mg of ALAs),
(C) "Hanamitsu Drink™" (contains 5 or 10 mg of ALAs, a product generally marketed by the present applicants) for each test subject, ingested in the range of 10 mg-150 mg total.

(A) The body condition "after alcohol consumption on the day of alcohol consumption" ("after alcohol consumption (same day)" in Table 5) and (B) the body condition on "the morning after the day of alcohol consumption" ("morning after alcohol consumption" in Table 5) were quantified with the following scores. In other words, a five-step evaluation (0: no indication, 1: mild, 2: moderate, 3: severe, and 4: profound) was performed for each test subject in regards to the following ten items (a-j) which are hangover symptoms. Then, evaluation values (0-4) for each item were summed for each test subject. The results are described in Table 5 as the "total score" showing hangover symptoms.

a. Headache
b. Retching/vomiting
c. Sleep disorder
d. Thirst
e. Perspiration
f. Trembling
g. Sensitivity to light/sound
h. Difficulty in concentrating
i. Anxiety/depression
j. Lassitude/weakness The summary of the above experiments are shown in Table 5 below.

TABLE 5

| test subject | Total amount of alcohol consumption (mL) | Presence or absence of ALAs ingestion | Amount of ALAs ingestion (mg) At the start of alcohol consumption | Amount of ALAs ingestion (mg) After the end of alcohol consumption | Total amount of ALAs ingestion (mg) | Total score After alcohol consumption (same day) | Total score Morning after alcohol consumption |
|---|---|---|---|---|---|---|---|
| 1 | 117 | X | 0 | 0 | 0 | 12 | 10 |
|   | 190 | ○ | 100 | 0 | 100 | 9 | 7 |
| 2 | 25 | X | 0 | 0 | 0 | 5 | 0 |
|   | 60 | ○ | 10 | 0 | 10 | 9 | 2 |
| 3 | 25 | X | 0 | 0 | 0 | 0 | 0 |
|   | 25 | ○ | 50 | 0 | 50 | 0 | 0 |
| 4 | 45 | X | 0 | 0 | 0 | 19 | 3 |
|   | 45 | ○ | 50 | 0 | 50 | 0 | 0 |
| 5 | 14 | X | 0 | 0 | 0 | 4 | 3 |
|   | 14 | ○ | 0 | 50 | 50 | 0 | 0 |
| 6 | 79 | X | 0 | 0 | 0 | 0 | 0 |
|   | 79 | ○ | 50 | 0 | 50 | 0 | 0 |
| 7 | 70 | X | 0 | 0 | 0 | 3 | 3 |
|   | 70 | ○ | 10 | 10 | 20 | 1 | 1 |
| 8 | 129 | X | 0 | 0 | 0 | 9 | 9 |
|   | 129 | ○ | 150 | 0 | 150 | 0 | 1 |
| 9 | 75 | X | 0 | 0 | 0 | 0 | 2 |
|   | 75 | ○ | 100 | 0 | 100 | 0 | 1 |
| 10 | 50 | X | 0 | 0 | 0 | 1 | 1 |
|   | 50 | ○ | 100 | 0 | 100 | 1 | 1 |

TABLE 5-continued

| test subject | Total amount of alcohol consumption (mL) | Presence or absence of ALAs ingestion | Amount of ALAs ingestion (mg) At the start of alcohol consumption | Amount of ALAs ingestion (mg) After the end of alcohol consumption | Total amount of ALAs ingestion (mg) | Total score After alcohol consumption (same day) | Total score Morning after alcohol consumption |
|---|---|---|---|---|---|---|---|
| 11 | 108 | X | 0 | 0 | 0 | 0 | 1 |
|    | 108 | ○ | 50 | 0 | 50 | 0 | 0 |
| 12 | 88  | X | 0 | 0 | 0 | 6 | 5 |
|    | 25  | ○ | 50 | 0 | 50 | 3 | 3 |
| 13 | 75  | X | 0 | 0 | 0 | 2 | 3 |
|    | 75  | ○ | 100 | 0 | 100 | 0 | 0 |
| 14 | 75  | X | 0 | 0 | 0 | 1 | 3 |
|    | 75  | ○ | 100 | 0 | 100 | 0 | 2 |
| 15 | 25  | X | 0 | 0 | 0 | 0 | 0 |
|    | 25  | ○ | 50 | 0 | 50 | 0 | 0 |

As apparent from the above Table 5:

(i) For each test, subject, when the total amount of alcohol consumption is the same, hangover symptoms were improved and a prophylactic effect of hangovers was seen (1) when ALAs was ingested compared to (2) when ALAs was not ingested for "after alcohol consumption (same day)" as well as for "morning after alcohol consumption" (test subjects 4, 5, 7-9, 11, 13, and 14).

(ii) Alcohol consumption at an amount more than usual was possible by ingesting ALAs "at the start of alcohol consumption" (test subjects 1 and 2). Moreover, in such a case, compared to when the usual amount of alcohol was consumed without ingesting ALAs, hangover symptoms were surprisingly mostly reduced even though the amount of alcohol consumption was more than usual (test subjects 1 and 2).

(iii) Hangover symptoms were generally improved and a prophylactic effect of hangovers was seen when ALAs was ingested only "at the start of alcohol consumption" (test subjects 1-4, 6, and 8-15) and when ALAs was ingested only "after the end of alcohol consumption" (test subject 5), as well as when ALAs was ingested both "at the start of alcohol consumption" and "after the end of alcohol consumption" (test subject 7).

(iv) Hangover symptoms were improved and a prophylactic effect of hangovers was seen even when a small amount of ALAs (10 mg) was ingested each of "at the start of alcohol consumption" and "after the end of alcohol consumption" (test subject 7).

(v) For test subjects who showed no hangover symptoms without ingesting ALAs, no hangover symptoms manifested even when ALAs was administered (test subjects 3, 6, and 15).

INDUSTRIAL APPLICABILITY

The agent of the present invention can be advantageously utilized as a hangover prophylactic and/or therapeutic agent.

The invention claimed is:

1. A method of treating a hangover in a subject in need thereof comprising administering to said subject a therapeutic agent comprising a compound of Formula I:

   (Formula I) or a salt thereof, wherein $R^1$ is a hydrogen atom or an acyl group, and $R^2$ is a hydrogen atom, a linear or branched alkyl group, a cycloalkyl group, an aryl group, or an aralkyl group, thereby treating the hangover in said subject.

2. The method according to claim 1, wherein
$R^1$ is selected from the group consisting of a hydrogen atom, an alkanoyl group having 1-8 carbons, and an aroyl group having 7-14 carbons, and
$R^2$ is selected from the group consisting of a hydrogen atom, a linear or branched alkyl group having 1-8 carbons, a cycloalkyl group having 3-8 carbons, an aryl group having 6-14 carbons, and an aralkyl group having 7-15 carbons.

3. The method according to claim 1, wherein
$R^1$ is selected from the group consisting of a hydrogen atom, a formyl group, an acetyl group, a propionyl group, and a butyryl group, and
$R^2$ is selected from the group consisting of a hydrogen atom, a methyl group, an ethyl group, a propyl group, a butyl group, and a pentyl group.

4. The method according to claim 1, wherein
$R^1$ is a hydrogen atom, and
$R^2$ is selected from the group consisting of a hydrogen atom, a methyl group, an ethyl group, a propyl group, a butyl group, and a pentyl group.

5. The method according to claim 1, wherein
$R^1$ is a hydrogen atom, and
$R^2$ is a hydrogen atom.

6. The method according to claim 1, wherein said therapeutic agent further comprises one or two or more types of metals.

7. The method according to claim 6, wherein said metal is selected from the group consisting of iron, magnesium, zinc, nickel, vanadium, copper, chromium, molybdenum, and cobalt.

8. The method according to claim 7, wherein said metal is selected from the group consisting of iron, magnesium, and zinc.

9. The method according to claim 8, wherein said metal is iron.

10. The method according to claim 9, wherein said iron is sodium ferrous citrate.

11. A method of reducing the risk of the occurrence of a hangover in a subject in need thereof comprising administering to said subject a prophylactic agent comprising a compound of Formula I:

   (Formula I) or a salt thereof, wherein $R^1$ is a hydrogen atom or an acyl group, and $R^2$ is a hydrogen atom, a linear or branched alkyl group, a cycloalkyl group, an aryl group, or an aralkyl group, thereby reducing the risk of the occurrence of the hangover in said subject.

12. The method according to claim 11, wherein
$R^1$ is selected from the group consisting of a hydrogen atom, an alkanoyl group having 1-8 carbons, and an aroyl group having 7-14 carbons, and
$R^2$ is selected from the group consisting of a hydrogen atom, a linear or branched alkyl group having 1-8 carbons, a cycloalkyl group having 3-8 carbons, an aryl group having 6-14 carbons, and an aralkyl group having 7-15 carbons.

13. The method according to claim 11, wherein
$R^1$ is selected from the group consisting of a hydrogen atom, a formyl group, an acetyl group, a propionyl group, and a butyryl group, and
$R^2$ is selected from the group consisting of a hydrogen atom, a methyl group, an ethyl group, a propyl group, a butyl group, and a pentyl group.

14. The method according to claim 11, wherein
$R^1$ is a hydrogen atom, and
$R^2$ is selected from the group consisting of a hydrogen atom, a methyl group, an ethyl group, a propyl group, a butyl group, and a pentyl group.

15. The method according to claim 11, wherein
$R^1$ is a hydrogen atom, and
$R^2$ is a hydrogen atom.

16. The method according to claim 11, wherein said prophylactic agent further comprises one or two or more types of metals.

17. The method according to claim 16, wherein said metal is selected from the group consisting of iron, magnesium, zinc, nickel, vanadium, copper, chromium, molybdenum, and cobalt.

18. The method according to claim 17, wherein said metal is selected from the group consisting of iron, magnesium, and zinc.

19. The method according to claim 18, wherein said metal is iron.

20. The method according to claim 19, wherein said iron is sodium ferrous citrate.

\* \* \* \* \*

UNITED STATES PATENT AND TRADEMARK OFFICE
CERTIFICATE OF CORRECTION

PATENT NO. : 10,022,345 B2
APPLICATION NO. : 14/954171
DATED : July 17, 2018
INVENTOR(S) : Tanaka et al.

Page 1 of 1

It is certified that error appears in the above-identified patent and that said Letters Patent is hereby corrected as shown below:

In the Specification

Column 5, Line 67: Please correct "diaramonium" to read -- diammonium --

Column 6, Line 56: Please correct "3000 rag" to read -- 3000 mg --

Signed and Sealed this
Sixteenth Day of October, 2018

Andrei Iancu
*Director of the United States Patent and Trademark Office*